United States Patent [19]

Semm

[11] Patent Number: 5,261,888
[45] Date of Patent: Nov. 16, 1993

[54] TROCAR SLEEVE

[75] Inventor: Horst K. Semm, München, Fed. Rep. of Germany

[73] Assignee: WISAP-Gesellschaft fur wissenschaftlichen Apparatebau mbH, Sauerlach, Fed. Rep. of Germany

[21] Appl. No.: 596,158

[22] Filed: Oct. 11, 1990

[30] Foreign Application Priority Data

Dec. 18, 1989 [DE] Fed. Rep. of Germany ....... 8914955

[51] Int. Cl.$^5$ .............................................. A61M 25/00
[52] U.S. Cl. ...................................... 604/164; 604/264; 604/158
[58] Field of Search ............... 604/158, 161, 162, 163, 604/164, 165, 169, 170, 51, 52, 53, 264

[56] References Cited

U.S. PATENT DOCUMENTS

| | | |
|---|---|---|
| 2,001,638 | 5/1935 | Tornsjo . |
| 4,431,426 | 2/1984 | Groshong et al. ................... 604/164 |
| 4,535,773 | 8/1985 | Yoon . |
| 4,769,018 | 9/1988 | Wilson ................................ 604/158 |
| 4,969,875 | 11/1990 | Ichikawa ............................ 604/164 |
| 5,011,473 | 4/1991 | Gatturna ............................ 604/164 |
| 5,059,186 | 10/1991 | Yamamoto et al. ................. 604/167 |

FOREIGN PATENT DOCUMENTS

| | | |
|---|---|---|
| 7513482 | 8/1975 | Fed. Rep. of Germany . |
| 2721012 | 12/1977 | Fed. Rep. of Germany . |
| 2835812 | 2/1980 | Fed. Rep. of Germany . |
| 1064445 | 5/1954 | France ................................ 604/158 |
| 1430092 | 3/1976 | United Kingdom ................ 604/158 |
| 2048686 | 12/1980 | United Kingdom . |

Primary Examiner—John G. Weiss
Attorney, Agent, or Firm—Keck, Mahin & Cate

[57] ABSTRACT

A trocar sleeve with a proximal main body having an axial, through opening and a distal end connected to the main body permits operationally reliable and easy working, if the sleeve is connected in a detachable and in particular manually replaceable manner to the main body.

19 Claims, 2 Drawing Sheets

TROCAR SLEEVE

BACKGROUND OF THE INVENTION

The invention relates to a trocar sleeve or cannula with a proximal main body having an axial through opening and with a distal sleeve connected to the main body.

Trocar sleeves of this type are generally known in endoscopic surgery. The trocar sleeves have an essentially one-piece construction, a cylindrical sleeve being soldered or bonded onto or into the proximal main body. The latter, which is the most complicated and therefore cost-intensive part of the trocar sleeve, generally has connections for surgical or optical appliances and gas supplies. It is also standard practice to have a manually adjustable or automatically closing valve for preventing a gas exchange between the interior of the body and the external atmosphere.

These trocar sleeves are traversed by a conically tipped or pointed trocar and are then inserted into the interior of the body, e.g. by perforating the abdominal wall. The trocar sleeve tip is bevelled, so that there is a lower perforation resistance on perforating the abdominal wall. After inserting the distal end of the trocar sleeve into the interior of the body, the trocar is withdrawn from the trocar sleeve, so that the latter constitutes a closable opening with respect to the body interior, through which it is possible to introduce into the latter optical or surgical instruments. Often trocar sleeves are provided with a connection for a gas supply, particularly $CO_2$, so as to raise the abdominal wall by producing an overpressure in the body interior and thereby obtain free accessibility to the internal organs.

In abdominal surgery operations surgical instruments, such as forceps, loops and scissors are introduced into the body interior through the trocar sleeve. The actuating or operating members of said instruments are axially oriented in the inoperative position, so that they can be easily introduced through the trocar sleeve. On drawing out operatively removed tissue fragments, e.g. with biopsy or claw forceps, it is standard practice to draw the forceps with the grasped tissue in the not completely closed state and with a varying amount of force into the sleeve, so that the forceps are necessarily closed to the diameter at the distal edge of the sleeve making it possible to draw the forcep mouth with gripped tissue into the trocar sleeve.

As a result the distal end of the sleeve is widened or expanded and then radially projects over the cylindrical trocar, which can lead to a traumatic action, because the widened area can perforate the tissue layers in knifelike manner. The bevelled, distal edge of the sleeve can also become blunt as a result of contact with the actuating members, which is very disadvantageous for a subsequent atraumatic sliding through the tissue, particularly in the case of a Z stitch.

The risk with sleeves soldered into the main body and hitherto normally with soft solder has been that after several uses and multiple sterilizations the soldered joints become brittle and the complete sleeve broke off at the soldered joint. As in the known trocar sleeves the proximal end thereof was almost strictly cylindrical, there was also a risk that in the case of a damaged soldered joint, the sleeve might slide into the interior of the body.

In order to avoid such risks, the one-piece trocar sleeve, i.e. the main body and the sleeve, had to be sent back to the manufacturer, so that the damaged sleeve could be unsoldered from the main body and replaced by a new sleeve. As an untight soldered joint between the sleeve and the main body can lead to a pressure drop in the body interior during the operation and possible complications must be eliminated from the outset, it is necessary to keep in stock a comparatively large number of reserve trocar sleeves. In addition, flexibility was also required with respect to the different trocar sleeve lengths. Moreover, the soldering in and out of sleeves constitutes a considerable cost factor.

SUMMARY OF THE INVENTION

The object of the invention is to so construct a trocar sleeve of the aforementioned type that it ensures an axially aligned, reliable seating of the sleeve on the main body and a simple, inexpensive sleeve replacement is possible. In the case of a trocar sleeve of the aforementioned type, this object is achieved according to the invention that the sleeve is connected in a detachable manner with the main body.

As a result of the inventive idea, in the case of damage to the sleeve, it can be released e.g. manually by simply unscrewing the screw cap and replaced by a new one. This easy replacement obviously is also possible in situations where the surgeon finds that he requires a longer or shorter sleeve for the complete trocar sleeve, in order to be able to carry out the operation with maximum safety.

Obviously better sterilization possibilities are provided by this simple connection between the main body and the sleeve. The idea even makes it possible to use sleeves with different diameters, provided that it is ensured that the proximal flanging or beading of the sleeve leads to a reliable, tight connection and preferably a self-centring connection with the main body. The axial alignment of the sleeve with the opening in the main body must always be ensured.

In an advantageous further development of the invention the proximal end of the sleeve is beaded and surrounded by a screw cap engaging behind the beading, which can be fixed positively and/or non-positively to the main body. This connection not only ensures a rapid replaceability of the sleeve, but also a much more reliable seating thereof on the main body. As a result of the beading and the screw cap engaging behind the same, the sleeve is also prevented from sliding into the body.

The invention also makes it possible to connect a main body to sleeves of varying length, which contributes to reducing expenditure for surgical instruments.

The connection between the sleeve and the screw cap is preferably provided by a thread. However, other fastenings are also possible, such as a plug-in or bayonet catch.

According to an advantageous further development of the invention the screw cap has two axially successively arranged circumferential areas, whereof one is constructed as a connecting area to the main body and the other as a grip or gripping area. Thus, a manual sleeve change can be performed very rapidly.

Since in the case of abdominal surgery the interior of the body is under a slight overpressure with respect to the atmosphere, it is necessary for the connection between the main body and the sleeve to be gas-tight. Thus, according to an advantageous further development of the invention, the main body has an annular bearing surface against which the beading is sealingly pressed by the screw cap. The screw cap in particular simultaneously ensures an exact axial orientation with the axial opening in the main body.

Appropriately the screw cap surrounds the sleeve with an approximate sliding fit, which ensures a good centring and reliable seal in the main body.

In order to bring about a further sealing improvement, a sealing ring can be fitted between the proximal sleeve end and the main body. This sealing ring is then preferably located between the bearing surface of the main body and the beading of the sleeve.

If the sleeve is constructed as a circular cylindrical tube with a distal bevel, the perforation resistance of the trocar sleeve on perforating the abdominal wall is particularly low. The circular cylindrical construction also permits a reliable centring on the main body.

As a result of the rapid, manual interchangeability of the sleeve, it is possible to rapidly adapt the trocar sleeve to any abdominal wall thickness, so that it is unnecessary to keep a large supply of relatively expensive, complete, but varyingly long trocar sleeves. In addition, the invention always keeps available sharp sleeves or trocar tips or points, so that traumatic effects of the type indicated hereinbefore are obviated. It is made virtually impossible for the sleeve to slip into the body on the one hand due to the proximal beading on the sleeve and on the other as a result of the radial size of the screw cap. Thus, the invention leads to considerable improvements compared with the hitherto used trocar sleeves with respect to the reliability of said sleeve, their easy manipulation and also their costs.

Advantageous further developments of the invention from the subject matter of subclaims.

BRIEF DESCRIPTION OF THE DRAWINGS

The invention is described in greater detail hereinafter relative to the drawings, wherein show.

DETAILED DESCRIPTION OF THE PREFERRED EMBODIMENT

Figure 1:
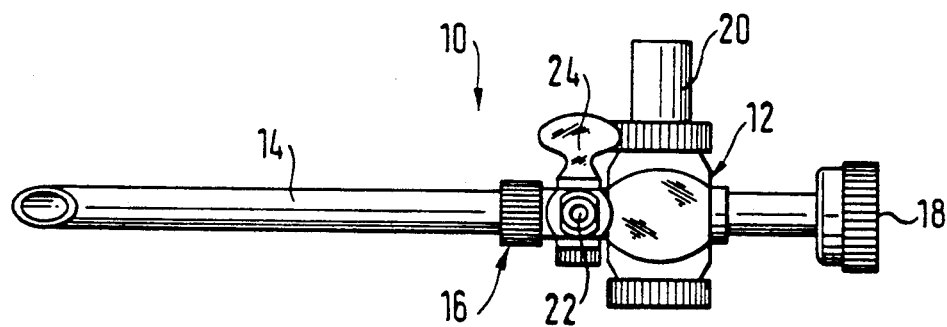
FIG. 1: A side view of a trocar sleeve with a sleeve screwed by a screw cap to a main body.

The trocar sleeve 10 comprises a main body 12 and a sleeve 14, which is fixed at its proximal end by means of a screw cap 16 to the main body. The main body 12 has an axial opening 18 (FIG. 2), whose axis is precisely aligned with the axis of the sleeve 14.

In the present embodiment the trocar sleeve 10 has a valve pretensioned in the closed position and which can be opened by pressure on the valve shaft 20, so that surgical instruments can be passed through the axial opening 18.

Figure 2:
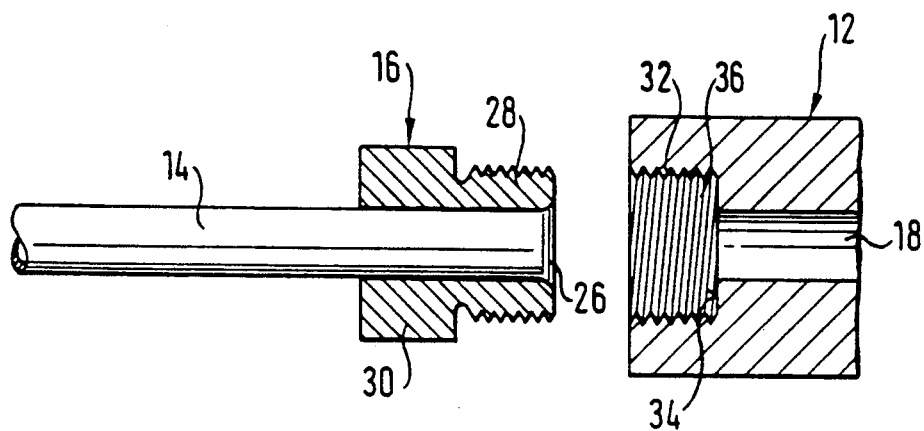
FIG. 2: A longitudinally sectioned, enlarged detail of the connection point between the main body and the sleeve of FIG. 1.

FIG. 2 shows the connection between the sleeve 14 and the main body 12 in detail. The sleeve 14 has at its proximal end a beading or flanging 26 behind which engages the screw cap 16, which is axially subdivided into two areas. The proximal part 28 is constructed as a connection area with an external thread. The distal part 30 of the screw cap 16 is constructed as a gripping area and is provided on its circular cylindrical outer circumference with a milled edge, so as to facilitate the screwing of the external thread 28 into an internal thread 32 formed on the main body 12. When the screw cap 16 is screwed into the main body 12, the beading 26 is pressed by the screw cap 16 against an annular, radial bearing surface 34, which is located in the main body at the end of a widened screwing area 36 with the internal thread 32. This leads to a good seal at the connection point between the sleeve 14 and the main body 12.

The sleeve 14 and the screw cap 16 are circular cylindrical and the screw cap 16 surrounds the sleeve 14 with a sliding fit. This leads to a good centring of the sleeve 14 on the main body 12, so that the axial opening 18 in the latter and the sleeve 14 are precisely aligned. This is important, so that no edge is formed at the connection point between the sleeve 14 and the main body 12, at which surgical or optical instruments could get caught or be damaged.

As a result of the inventive connection of the sleeve 14 and the main body 12, the operational reliability and handling of the trocar sleeve are significantly improved. The apparatus expenditure on surgical instruments can also be reduced, because there is no need to provide a complete trocar sleeve for each sleeve length and diameter.

Figure 3:
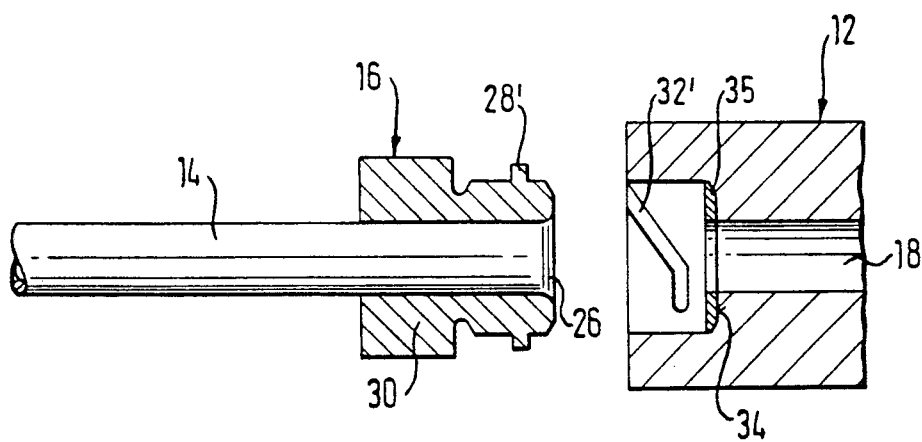
FIG. 3: A longitudinally sectioned, enlarged detail of the connection point between the main body and the sleeve of FIG. 1 with a bayonet catch.

FIG. 3 shows a connection between the sleeve 14 and the main body 12 in another embodiment of the invention.

Technical features which are identical to the embodiment according to FIG. 2 are indicated with identical reference numerals.

The proximal part 28' of the sleeve 14 is constructed as a connection area for a bayonet catch. This connection area has two pins on radially opposite sides of the screw cap 16. The pins engage in slideways 32' which are disposed in a complementary connection area of the main body 12. The screw cap 16 is pressed against a sealing ring 35, which is disposed on an annular radial bearing surface 34, located in the main body at the end of a widened connection area with the slideways 32'.

What we claim is:

1. A trocar sleeve comprising a proximal main body having an axial through-bore, a distal sleeve, and a detachable connection between the distal sleeve and the main body, wherein the distal sleeve has a proximal end formed with a bead and wherein a cap is mounted on said proximal end engaging the bead, the cap being detachably attached to the main body to provide said connection.

2. A trocar sleeve according to claim 1, wherein the cap has a thread which engages in a complimentary thread on the main body.

3. A trocar sleeve according to claim 1, wherein the cap is attached to the main body by a bayonet catch.

4. A trocar sleeve according to claim 1, wherein the cap has two axially adjacent circumferential areas, one of said areas providing the connection with the main body and the other said areas providing a gripping area.

5. A trocar sleeve according to claim 4, wherein the gripping area is provided with a roughened external surface.

6. A trocar sleeve according to claim 1, wherein the main body has an annular surface against which the bead is pressed into sealing engagement by the cap.

7. A trocar sleeve according to claim 1, wherein the distal sleeve is axially aligned with said through-bore in the main body by means of a screw cap.

8. A trocar sleeve according to claim 1 including a sealing ring fitted between the distal sleeve and the main body.

9. A trocar sleeve according to claim 1, wherein the distal sleeve comprises a circular cylindrical tube with a bevelled distal end.

10. A trocar sleeve comprising a proximal main body having an axial through-bore, a distal sleeve, and a detachable connection between the distal sleeve and the main body, wherein the distal sleeve has a proximal end formed with a bead, and a cap mounted on said proximal end engages the bead, the cap being detachably attached to the main body to provide said connection, wherein the cap has a sliding fit on the distal sleeve.

11. A trocar sleeve comprising
a proximal main body having an axial through-bore, and a distal sleeve having a proximal beaded end which is engaged by a cap having a sliding fit on said distal sleeve and being attachable to said proximal main body to provide a detachable connection between said distal sleeve and said proximal main body,
said cap having two axially adjacent circumferential areas, one of said axially adjacent circumferential areas providing said detachable connection and the other providing a gripping area.

12. A trocar sleeve according to claim 11, wherein said gripping area is provided with a roughened external surface.

13. A trocar sleeve according to claim 11, wherein said main body has an annular surface against which the beaded end is pressed into sealing engagement by said cap.

14. A trocar sleeve comprising
a proximal main body having an axial through-bore and an annular surface around a distal end of said through-bore, and
a distal sleeve having a proximal beaded end which is engaged by a cap which has a sliding fit on said distal sleeve and being attachable to the proximal main body to press said beaded end into sealing engagement with said annular surface of said proximal main body, said cap having two axially adjacent circumferential areas, one of said axially adjacent circumferential areas providing a connection with said main body and the other providing a gripping area.

15. A trocar sleeve according to claim 14, wherein said cap has a thread which engages in a complementary thread on said main body.

16. A trocar sleeve according to claim 14, wherein said cap is attached to said main body by a bayonet catch.

17. A trocar sleeve according to claim 14, wherein said distal sleeve is axially aligned with said through-bore in said main body by means of a screw cap.

18. A trocar sleeve according to claim 14, including a sealing ring fitted between said distal sleeve and said main body.

19. A trocar sleeve according to claim 14, wherein said distal sleeve comprises a circular cylindrical tube with a bevelled distal end.

* * * * *